United States Patent
Blick et al.

(10) Patent No.: US 7,765,013 B2
(45) Date of Patent: Jul. 27, 2010

(54) NANO- AND MICRO-SCALE WIRELESS STIMULATING PROBE

(75) Inventors: Robert H. Blick, Madison, WI (US); Max G. Lagally, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 490 days.

(21) Appl. No.: 11/757,487

(22) Filed: Jun. 4, 2007

(65) Prior Publication Data

US 2008/0300663 A1 Dec. 4, 2008

(51) Int. Cl.
*A61F 2/00* (2006.01)
(52) U.S. Cl. .......................... 607/116; 607/62; 607/60; 607/573; 607/2
(58) Field of Classification Search ................ 607/60, 607/62, 116; 600/573
See application file for complete search history.

(56) References Cited

U.S. PATENT DOCUMENTS

2003/0078643 A1* 4/2003 Schulman et al. ........... 607/116
2004/0015205 A1* 1/2004 Whitehurst et al. .......... 607/48
2004/0122475 A1* 6/2004 Myrick et al. ................ 607/2
2006/0212097 A1* 9/2006 Varadan et al. .............. 607/62
2006/0282014 A1* 12/2006 Kipke et al. ................. 600/573

OTHER PUBLICATIONS

Prinz et al. "Application of semiconductor micro- and nanotubes in biology" Surface Science 532-535 (2003) 911-915.*
Wise et al. "Wireless Implantable Microsystems: High-Density Electronic Interfaces to the Nervous System" Proceedings of the IEEE, vol. 92 No. 1, Jan. 2004.*
Xu et al. "Cell-based biosensors based on light-addressable potentiometric sensors fro single cell monitoring" Biosensors and Bioelectronics 20 (2005) 1757-1763.*

* cited by examiner

*Primary Examiner*—Carl H. Layno
*Assistant Examiner*—Jon-Eric C. Morales
(74) *Attorney, Agent, or Firm*—Boyle Fredrickson, S.C.

(57) ABSTRACT

Untethered micro or nanoscale probes may be dispersed within tissue to be individually addressed through external electromagnetic radiation to create local electrical currents used for direct stimulation, alteration of cellular potentials, or the release or modification of contained or attached chemical compounds.

22 Claims, 2 Drawing Sheets

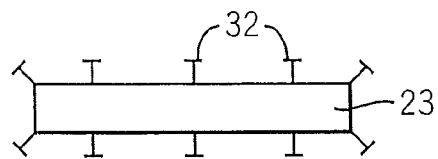
FIG. 5
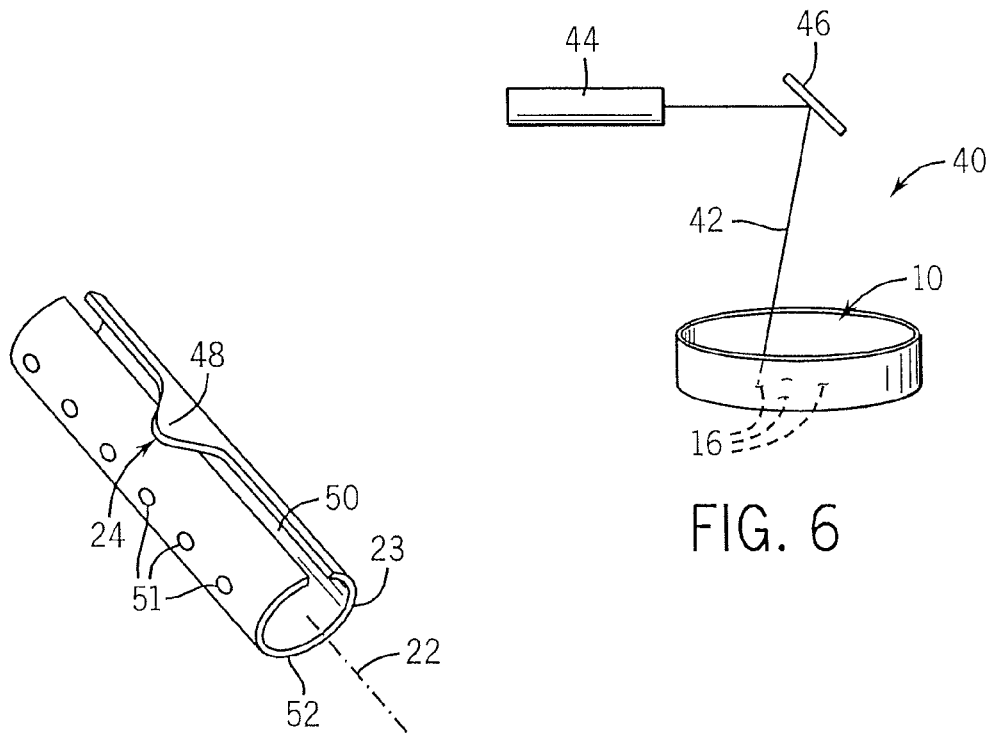
FIG. 6
FIG. 7
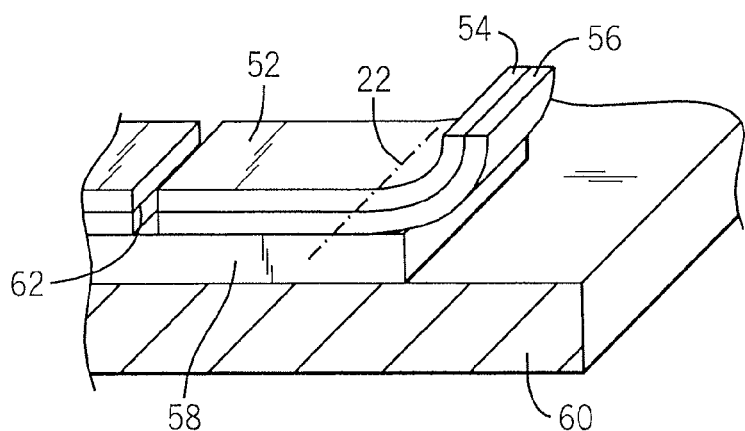
FIG. 8

NANO- AND MICRO-SCALE WIRELESS STIMULATING PROBE

STATEMENT REGARDING FEDERALLY SPONSORED RESEARCH OR DEVELOPMENT

This invention was made with United States government support awarded by the following agency: NSF 0520527. The United States has certain rights in this invention.

CROSS REFERENCE TO RELATED APPLICATION

1. Background of the Invention

The present invention relates to a method and apparatus for the manipulation of cellular-level activity and in particular to a small-scale wireless probe for electrical and/or chemical stimulation of living tissue.

The study of cellular activity, for example, the operation of neurons, may require localized stimulation of individual or small clusters of cells. This may be done through the use of fine electrodes inserted into or near the cells and connected by leads to external equipment. The cells may be stabilized with the tip of a pipette or by using an on-chip cell measurement system such as is commercially available from Nanion Technologies (www.nanion.de) or using a technology such as Neurochips offered by Infineon (www.infineon.com).

Such stabilization systems can be intrusive and may require a path through adjacent tissue to the stimulation site, and/or immobilization of the tissue, which, in some applications, may adversely affect the desired results. Interference between support structure for adjacent electrodes or pipettes can prevent close electrode spacing or placement of the electrodes in multiple dimensions. Such electrode systems can be impractical for long-term placement in living organisms.

2. Summary of the Invention

The present invention provides freely dispersible micro- or nano-scale probes that may be activated without a direct wired connection. The probes may receive electromagnetic radiation, for example light, and convert that light to a local electric potential and subsequently to an electrical-current flow. The current flow may be used directly for electrical stimulation or to trigger a chemical or mechanical release of chemical compounds held by the probes or activation of a biological system such as ion channels. In one embodiment the probes may be small tubes of strained semiconductor material that overlap upon themselves to form a heterojunction semiconductor device. In another embodiment the probes can be formed by junctions between different semiconducting nanoparticles.

Specifically then, the present invention provides a wirelessly stimulatable probe having a dispersible element attachable to tissue structure and substantially less than 100 micrometers in size. The dispersible element accepts electromagnetic radiation to produce an electrical current local to the dispersible element.

It is thus one aspect of the invention to provide for the local delivery of electrical current at extremely small scales for use in cellular research or novel therapies providing long-term electrical stimulation of neural cells.

The dispersible element may be a strain curved semiconductor membrane.

It is thus another aspect of the invention to provide both a material and a topology that provide at least one of: a sufficient surface area for the construction of integrated-circuit type microelectronics, a sufficient surface area or curved-surface area that may provide a carrier for bioactive chemical compounds, a desirable shape for an antenna or optical conduit, and/or an aspect ratio allowing the generation of an electrical dipole for electrical manipulation of the dispersible element in tissue.

The strain curved semiconductor membrane may be a tube having an overlap region comprising n and p type doped regions to form a heterojunction device.

It is thus one object of the invention to provide a simple method of fabricating a versatile p-n junction.

The p-n junction may be a photodiode.

It is thus another object of the invention to provide a simple method of fabricating a photodiode for the generation of local electrical currents.

The dispersible element may further include adhered chemicals activated by the electrical current.

It is another aspect of the invention to provide remotely controlled delivery of chemicals as triggered by the generated electrical current flow.

The dispersible elements may further include semiconductor circuitry activated by the electrical current.

It is thus another object of the invention to provide for a remote wireless triggering of more complex electrical circuitry contained on the dispersible element.

The dispersible element may include surface adhered biologically active chemicals.

It is another object of the invention to provide a dispersible element that is chemically compatible with the tissue or chemically targeted to particular tissue structures or types.

The invention may be used to produce a cellular scale addressable probe array having a plurality of dispersible elements attachable to spatially separated tissue structure, each dispersible element accepting an electromagnetic radiation to produce an electrical current local to the dispersible element. An electromagnetic radiation source may be steered to produce the electrical current local to a predetermined subset of the dispersible elements.

It is another object of the invention to provide for multidimensional stimulation of tissue without the need for connecting wires or interference among the connecting wires or connecting wires and tissue structure.

The electromagnetic radiation source is a laser.

It is another aspect of the invention to provide for a highly localized electromagnetic stimulation that may stimulate as few as a single dispersible element.

These particular objects and advantages may apply to only some embodiments falling within the claims and thus do not define the scope of the invention.

BRIEF DESCRIPTION OF THE DRAWINGS

FIG. 5 is a simplified diagram of the tube of FIG. 2 with a surface coating of chemicals used for targeting the probe to a particular structure;

FIG. 6 is a simplified diagram of the elements of a scanning laser system that may be used to selectively activate the probes of FIG. 1;

FIG. 7 is a figure similar to that of FIG. 2 showing an alternative configuration of the probe in which the seam is reduced to a point contact; and FIG. 8 is a perspective view of one process for creating the tubes of FIGS. 2 and 7 using strained semiconductor membranes released from a substrate by etching.

DETAILED DESCRIPTION OF THE PREFERRED EMBODIMENT

Figure 1:
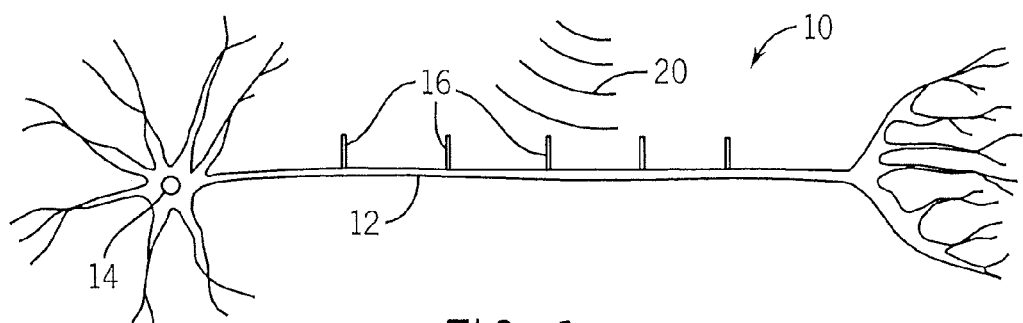
FIG. 1 is a schematic representation of a nerve cell showing wireless probes of the present invention arrayed along a neural pathway.

Referring now to FIG. 1, the direct stimulation of neural tissue 10 for research or therapeutic purposes may require electrical stimulation at various locations along an axon 12 of a neural cell 14. Such stimulation may be accomplished by attaching a series of floating stimulating probes 16 to the axon 12 at the desired sites. The term floating, as used herein, means untethered by signal leads.

The probe 16 may be placed at the desired sites in the tissue by direct mechanical manipulation, for example with forceps or micromanipulators, or steered to the sites using an electrostatic field operating on an electrical dipole formed in the probes 16. Importantly, however, once the probes 16 are positioned, they do not need electrical or mechanical connection to an external device.

As will be described in greater detail below, when the probes 16 are properly positioned, they may be stimulated by electromagnetic radiation 20, including light or a radiofrequency electromagnetic field, to produce a local current flow. In the example of FIG. 1, this local current flow may provide a direct electrical stimulation to the axon 12 to which the probes 16 are attached. Because the probes 16 do not require supporting structure or connecting leads, they may be freely placed in three dimensions within the tissue and may allow free movement or growth of the tissue.

Figure 2:
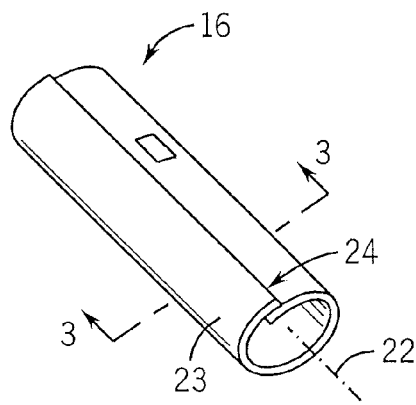
FIG. 2 is a perspective view of a single wireless probe of FIG. 1 having a tubular form with an overlapped axial seam.
Figure 3:
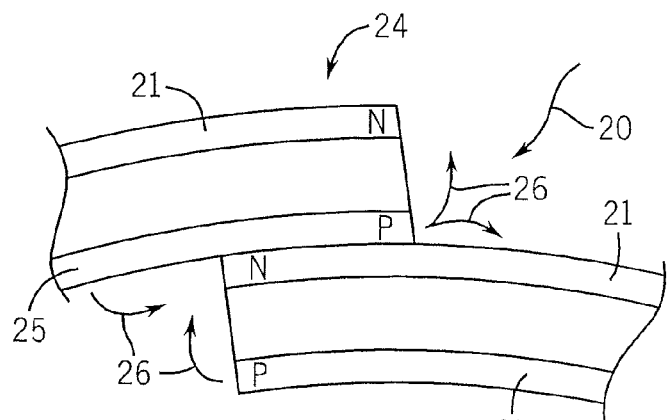
FIG. 3 is a cross-section along line 3-3 of FIG. 2 showing a heterojunction formed at the seam of the tube of FIG. 2 such as may be used to create a photodiode.

Referring to FIG. 2, in a preferred embodiment each of the probes 16 is formed of a tube 23 of semiconducting membrane rolled about an axis 22 to overlap along a seam 24 extending parallel to the axis 22. Referring also to FIG. 3, the outer surface of the tube 23 may be doped with an electron donor to create a so-called n-material 21 while the inner surface of the tube may be doped with an electron acceptor to create so-called p-material 25. The rolling of the semiconducting membrane into the tube 23 creates at the interface of the seam 24 an abutment of p-material 25 and n-material 21 producing a heterojunction p-n device 27.

Figure 4:
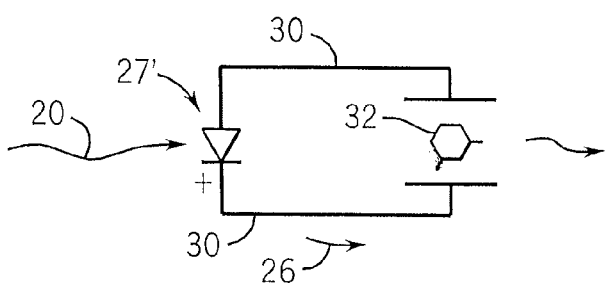
FIG. 4 is a schematic representation of the tube of FIG. 2 showing use of the electrical current generated by the photodiode to activate chemicals attached to or contained in the tube of the probe.

Referring now to FIGS. 3 and 4, as is generally understood in the art, the heterojunction p-n device 27 may be operated as a photodiode 27'. Photodiodes 27' are well known devices that may be used either in a photoconductive mode, in which their conductivity changes as a function of received light or, in this embodiment, in a photovoltaic mode, in which they generate a current 26 flowing from an effective or constructed ohmic contact between the p-material 25 and surrounding tissue and an effective or constructed ohmic contact between the surrounding tissue and the n-material 21. This current flow may be outside of the tube 23 or inside of the tube 23 as controlled by the addition of insulating materials to the inside and/or the outside of the tube 23 as may be desired.

In addition, or alternatively, conductive paths and ohmic contacts may be formed at particular locations on the surface of the tube 23, for example, using standard photolithographic integrated circuit techniques, as will be described. These conductive paths may be used to channel the current flows to particular locations on the tubes 23, for example axial ends of the tubes 23, as may be desired. Referring again to FIG. 2, the electrical currents 26 as channeled may be used to power other electrical devices 28, for example FET transistors, formed by integrated circuit techniques on the inner or outer surface of the tube 23 as may be desired. In this case, the effective surface area of the tube 23 provides larger fabrication areas for such integrated circuits such as may not be available in a solid structure of similar outside dimensions.

If a piezoelectric material is used together with the semiconductor membrane, then the electricity from generated by the heterojunction may be used to create mechanical motion or movement of the probe 16 to maneuver probe 16, release chemicals therefrom, or provide mechanical stimulation on an extremely small and localized scale.

Referring now to FIG. 4, photodiode 27' may alternatively or in addition provide for conductive pathways 30 conveying the current 26 to chemical substances 32 held on the surface of the tube 23 or within the tube 23. The currents may activate the chemical substances 32 or generate new chemical substances (e.g., by promoting electrochemical reactions) or may release the chemical substances 32, for example using electrophoresis techniques or by modification of mediating chemical compounds. Alternatively the electrical current can be used to create local heating of the tube 23 causing it to unroll to release its chemical contents. The chemicals conjugated to the probes 16 may include enzymes, antibodies, polysaccharides, and the like.

In this way the electromagnetic radiation 20 may be used not only for electrical stimulation but also for the release of chemical compounds 32 on a local basis. Because the probes 16 are wireless, they may be implanted within a cell membrane to interact with internal cellular mechanisms.

Referring now to FIG. 5, the tube 23 may be further coated with chemical compounds, such as polymers, that improve its biocompatibility, or linkers to proteins, such as epoxide or aldehyde groups for chemical attachment of biomolecules such as DNA, or antibodies, or linkers to sugar components in phospholipid membranes. The compounds can target the probes 16 to particular locations or integrate the probes 16 into particular cellular processes. This functionalization of the surface of the tubes 23 may, for example, use the techniques described in U.S. Pat. No. 6,402,899 by Denes et al. entitled "Process for intercalation of spacer molecules between substrates and active biomolecules" issued Jun. 11, 2002, and hereby incorporated by reference.

Referring to FIG. 6, the probes 16 of the present invention may be employed with a scanning system 40 for selectively irradiating particular ones of the probes 16 to provide for selective activation of different probes 16. In the embodiment depicted, cell structure, for example neural tissue 10, may be exposed to a focused laser beam 42 from a laser source 44. The laser beam 42 from the laser source 44 is steered to a particular probe 16 or group of probes 16 by a mirror assembly 46 providing for two axes of control, such mirror assemblies being well known in the art. The laser beam 42 may be modulated to be turned on only at the site of a probe 16 where activation is required, for a controllable amount of time.

Additional laser beams 42 may be used additively and/or at different angles to attain multiple dimensions of discrimination particularly for probes 16 that may be arrayed in a line from a mirror assembly 46 or that are blocked from one mirror assembly by tissue structure. The scanning system 40 in this way may permit three-dimensional dispersion of the probes 16 within a cell matrix limited only by the ability of the electromagnetic radiation to penetrate through the layers of the cells.

While light is considered to be the principal source of electromagnetic radiation for activating the probes 16, it will be recognized that the tubular structure of the probe 16 also lends itself to the reception of lower-frequency electromagnetic radiation, in which case the tube 23 may form an antenna or resonant structure tuned to a particular frequency range. This tuning allows radiation to be steered to particular probes 16 by frequency multiplexing. Techniques of phased array beam steering may also be used.

Referring now to FIG. 7, many variations in the structures of the tube 23 may be envisioned, for example, in which the membrane 52 includes a tongue 48 at the seam 24 so that the area of overlap at the seam 24 is limited to the tongue 48, and a channel 50 is opened along the axis 22 allowing improved or different flow of materials into and out of the center of the tube 23. The tongue 48 may be used to localize and enhance the voltage drop across the heterojunction and may be placed alternatively at one end of the tube 23 to be proximate to the tissue to which the tube is attached. The outside of the tube 23 may be decorated with quantum dots 51 providing identification and improved location of the probes 16.

Referring to FIG. 8, fabrication of the tubes of the probes 16 may be performed by standard integrated circuit techniques in which a semiconductor membrane 52 includes two layers of different materials 54 and 56, for example Si and SiGe alloy. The different materials create stress at the interface of the material that is resisted by an underlying sacrificial layer 58 attaching the membrane 52 to a substrate 60. In this planar state, the membrane 52 may be processed in a manner of standard integrated circuit construction including the doping of particular regions and the deposition of conductive pathways. When the sacrificial layer 58 is removed by etching, the natural stress between the materials 54 and 56 causes them to curl about axis 22. An etched cut 62 allows the membrane 52 to be wholly released when the sacrificial layer 58 is fully etched away providing for the dispersible probe 16 of the present invention. A description of this process and citations to some techniques and applications for this process are described generally in Science, vol. 313, Jul. 14, 2006. The length of the tubes may be in the micro range (e.g., less than 100 micrometers) or nano range (e.g., less than 100 nanometers).

Alternatively, heterojunctions may be generated in individual semiconductor nanoparticles by doping the semiconductor to form different n- and p-regions, or by assembling two nanoparticles together, each having a different doping, so that the heterojunction is formed at their mechanical interface.

The present invention is not limited solely to electromagnetic stimulation but may also be used in combination with mechanical excitation, for example, ultrasonic stimulation.

The electromagnetic stimulation may also be used as part of a sensing process to power sensors in the probes 16 that return faint electrical echoes much in the manner of RFID tags to provide for information about cellular processes. In the case of the laser excitation of the probes 16, local emission from the probes 16 may be detected such as may reveal information about the state of the probe 16 or its environment. The radiation will be highly directed and/or polarized as a result of the orientation and shape of probes 16, providing information about the probes 16 and/or distinguishing the local emissions of the probes 16 from other sources. Embedding other materials in the walls of the probes 16, e.g., quantum dots or fluorescent materials, can provide local radiator elements to enhance these effects.

It is specifically intended that the present invention not be limited to the embodiments and illustrations contained herein and the claims should be understood to include modified forms of those embodiments, including portions of the embodiments and combinations of elements of different embodiments as come within the scope of the following claims.

What we claim is:

1. A wirelessly stimulatable probe comprising:
an untethered, dispersible element attachable to tissue structure and substantially less than 100 micrometers in a longest dimension, the dispersible element absorbing electromagnetic radiation to produce an electrical current local to the dispersible element; energy of the electromagnetic radiation providing the sole source of electrical power for the dispersible element in interacting with the tissue structure.

2. The wirelessly stimulatable probe of claim 1 wherein the dispersible element is a strain curved semiconductor membrane.

3. The wirelessly stimulatable probe of claim 2 wherein the strain curved semiconductor membrane is a tube having an overlap region comprising n and p type doped regions to form a heterojunction device.

4. The wirelessly stimulatable probe of claim 3 wherein the heterojunction device is a photodiode.

5. The wirelessly stimulatable probe of claim 1 wherein the dispersible element is a semiconductor membrane providing abutting n and p type doped regions.

6. The wirelessly stimulatable probe of claim 1 wherein the dispersible element further includes adhered chemicals activated by the electrical current.

7. The wirelessly stimulatable probe of claim 1 wherein the dispersible elements further include semiconductor circuitry activated by the electrical current.

8. The wirelessly stimulatable probe of claim 1 wherein the dispersible element includes adhered chemicals providing for biological interaction.

9. The wirelessly stimulatable probe of claim 1 further including a probe feature re-emitting energy of the received electromagnetic radiation modified by the probe.

10. A cellular scale addressable probe array comprising:
a plurality of untethered, dispersible elements attachable to spatially separated tissue structure, the dispersible elements less than 100 micrometers in a longest dimension and absorbing electromagnetic radiation to produce an electrical current local to the dispersible element, energy of the electromagnetic radiation providing substantially the sole source of electrical power for the dispersible element in interacting with the tissue structure; and
an electromagnetic radiation source steerable to produce the electrical current local to a predetermined subset of the dispersible elements.

11. The cellular scale addressable probe array of claim 10 wherein the electromagnetic radiation source is a laser.

12. A method of wirelessly stimulating tissue structure comprising:
locating one or more untethered, dispersible elements substantially less than 100 micrometers in a longest dimension in the tissue structure; and
stimulating the elements with electromagnetic radiation to produce an electrical current local to the elements, the electrical current generated substantially solely from energy of the stimulating electromagnetic radiation absorbed by the dispersible elements.

13. The method of claim 12 wherein the elements are strain curved semiconductor membranes.

14. The method of claim 13 wherein the strain curved semiconductor membrane is a tube having an overlap region comprising n and p type doped regions to form a heterojunction device.

15. The method of claim 14 wherein the heterojunction devices are photodiodes.

16. The method of claim 12 wherein the elements are semiconductor membranes providing abutting n and p type doped regions.

17. The method of claim 12 wherein the elements further include adhered chemicals activated by the electrical current.

18. The method of claim 12 wherein the elements further include semiconductor circuitry activated by the electrical current.

19. The method of claim 12 wherein the elements include adhered chemicals providing for biological interaction.

20. The method of claim 12 including multiple elements and including the step of steering the electromagnetic radiation source among elements to produce the electrical current local to different subsets of the elements at different times.

21. The method of claim 20 wherein the electromagnetic radiation source is a laser.

22. The method of claim 20 further including the step of re-emitting energy of the accepted electromagnetic radiation as modified by the probe.

* * * * *